(12) United States Patent
Sauer et al.

(10) Patent No.: US 9,022,565 B2
(45) Date of Patent: May 5, 2015

(54) METHOD AND APPARATUS FOR CHECKING THE CENTERING OF SPECTACLES WORN BY A SPECTACLE WEARER

(75) Inventors: Ralf-Roland Sauer, Huettlingen (DE); Matthias Kubitza, Aalen (DE); Jésus Miguel Cabeza Guillén, Aalen (DE)

(73) Assignee: Carl Zeiss Vision GmbH, Aalen (DE)

(*) Notice: Subject to any disclaimer, the term of this patent is extended or adjusted under 35 U.S.C. 154(b) by 28 days.

(21) Appl. No.: 13/021,796

(22) Filed: Feb. 7, 2011

(65) Prior Publication Data
US 2011/0205487 A1 Aug. 25, 2011

Related U.S. Application Data

(63) Continuation of application No. PCT/EP2009/005812, filed on Aug. 11, 2009.

(30) Foreign Application Priority Data

Aug. 13, 2008 (DE) .......................... 10 2008 039 416

(51) Int. Cl.
*A61B 3/11* (2006.01)
*G02C 13/00* (2006.01)

(52) U.S. Cl.
CPC .............. *G02C 13/005* (2013.01); *A61B 3/111* (2013.01)

(58) Field of Classification Search
CPC ..... G02C 13/00; G02C 13/003; G02C 13/005
USPC ........... 359/204, 206, 246, 247; 351/204, 206
See application file for complete search history.

(56) References Cited

U.S. PATENT DOCUMENTS 6,286,957 B1 * 9/2001 Livnat ........................... 351/204
6,659,609 B2 12/2003 Mothes
(Continued)

FOREIGN PATENT DOCUMENTS

DE 100 33 983 A1 10/2001
DE 101 25 050 B4 12/2002
(Continued)

OTHER PUBLICATIONS

Sessner et al. WIPO Translation, Jan. 2008.*

*Primary Examiner* — Thomas K Pham
*Assistant Examiner* — Marin Pichler
(74) *Attorney, Agent, or Firm* — Harness, Dickey & Pierce, P.L.C.

(57) ABSTRACT

A method and an apparatus serve for checking the centering of spectacles worn by a spectacle wearer. The method comprises the steps of: a) measuring spectacle lenses mounted in a frame of the spectacles, wherein a position of permanent markings on the spectacle lenses is acquired relative to a coordinate system defined by the frame by means of an image recognition system; b) determining positions of nominal centering points, prescribed in a file, of the spectacle lenses in dependence on data of the spectacle lenses containing the position of the permanent markings; c) measuring physiological data of a spectacle wearer wearing the spectacles and determining positions of actual centering points of the spectacle lenses from the physiological data by means of a video centering instrument; d) determining the difference between the positions of the nominal centering points and the actual centering points; and e) comparing the difference to a prescribed difference threshold.

10 Claims, 2 Drawing Sheets

(56) References Cited

U.S. PATENT DOCUMENTS

| | | |
|---|---|---|
| 2003/0123026 A1* | 7/2003 | Abitbol et al. ............... 351/204 |
| 2006/0044509 A1* | 3/2006 | Fluegge et al. ............. 351/208 |
| 2007/0115429 A1 | 5/2007 | Divo |
| 2007/0118428 A1 | 5/2007 | Akiyama et al. |
| 2009/0021693 A1* | 1/2009 | Sessner et al. ............. 351/204 |
| 2009/0066914 A1* | 3/2009 | Moinard ..................... 351/204 |
| 2010/0220285 A1* | 9/2010 | Simmonds ................... 351/204 |

FOREIGN PATENT DOCUMENTS

| | | | |
|---|---|---|---|
| DE | 103 33 426 A1 | 2/2005 | |
| DE | 10 2006 033 491 A1 | 1/2008 | |
| FR | 2 900 246 | 10/2007 | |
| WO | WO/2008/009355 * | 1/2008 | ............ G02C 13/00 |
| WO | WO2008/009355 A1 | 1/2008 | |
| WO | WO 2008009355 A1 * | 1/2008 | |
| WO | WO2008/089995 A1 | 7/2008 | |

\* cited by examiner

METHOD AND APPARATUS FOR CHECKING THE CENTERING OF SPECTACLES WORN BY A SPECTACLE WEARER

CROSS-REFERENCE TO RELATED APPLICATIONS

The present application is a continuation of International Patent Application PCT/EP2009/005812, filed on Aug. 11, 2009 and published in German language, which International Patent Application claims priority under the Paris Convention from German Patent Application DE 10 2008 039 416.5, filed Aug. 13, 2008. The entire contents of these priority applications are incorporated herein by reference.

BACKGROUND OF THE INVENTION

The invention relates to a method for checking the centering of spectacles worn by a spectacle wearer.

The invention furthermore relates to an apparatus for checking spectacles worn by a spectacle wearer.

When a spectacle wearer purchases spectacles with optically effective spectacle lenses, faulty workmanship may occur during the production of the spectacles. By way of example, the left and right spectacle lenses may have been mixed up, or one or both spectacle lenses may have the wrong refractive power. Furthermore, the spectacle lenses may be wrongly centered.

While the first-mentioned faults can be identified relatively easily by measuring the spectacle lenses and comparing them to the prescription, it requires more effort to identify a wrong centering of the spectacle lenses.

These days, progressive lenses have a far reference point and a near reference point, which are determined for each progressive lens during production. These points cannot be identified on the spectacle lens. Furthermore, progressive lenses are provided with permanent markings, which are usually engraved by laser and just about visible to the unaided eye. The permanent markings are arranged on the spectacle lens at a predetermined relative position with respect to the far reference point and the near reference point and possibly also contain information relating to the specific spectacle lens.

When a spectacle wearer purchases spectacles, the spectacle lenses must be centered in the frame in relation to the individual pupil spacing and possibly also to the position of the corneal vertex of the spectacle wearer so that the spectacle lenses are correctly positioned in this frame in optical terms.

By way of example, this can be brought about by means of a video centering instrument, wherein the spectacle wearer puts on the desired frame and the position of the pupils of the spectacle wearer and the fit and shape of the frame are then registered by means of a frontal and a lateral camera. Such a video centering instrument is distributed by the applicant under the name "Video Infral RVT". The optimum position of the spectacle lenses in the frame is then calculated from the measured values, and the spectacle lenses are edged accordingly and inserted into the frame.

If no video centering instrument is available, the desired frame with optically neutral support discs are put onto the spectacle wearer by the optician and the latter manually marks the position of the centering points on the support discs relative to the position of the pupils. The optician can then use templates, provided to the optician by the spectacle-lens producers, to convert the manually applied markings into correct positioning of the spectacle lenses.

If there now is a wrong centering of the finished spectacles and the spectacle wearer lodges a complaint with his/her optician, then only manual procedures have been used to date for determining a possible centering error.

The optician firstly looks for the permanent markings on the spectacle lenses and marks them using a colored pen so they can be identified more easily. Then the aforementioned templates are used to draw on the far reference point and the near reference point, the spectacles are put on the spectacle wearer and checking takes place as to whether the actual reference points correspond to the drawn-on nominal reference points. To this end, use can be made of what is known as Victorin's method.

It is clear that this procedure is very cumbersome and is in turn inflicted with a risk of error. An additional difficulty in the case of modern spectacle lenses, which are provided with a dirt-repellent coating on the basis of the lotus effect, is that markings cannot be applied at all using the conventional colored pens.

DE 103 33 426 A1 discloses an apparatus by means of which permanent markings can be identified on spectacle lenses and the position of which permanent markings can be determined on the spectacle lens.

DE 10 2006 033 491 A1 discloses a centering instrument wherein engraving points are also determined, but only in the context of manual marking of saddle points.

SUMMARY OF THE INVENTION

The invention is therefore based on the object of improving a method and an apparatus of the kind mentioned at the outset to the extent that the aforementioned disadvantages are avoided. More particularly, provision should be made for a method and an apparatus, by which the checking of the centering is possible in an easier and more precise fashion.

According to the invention, a method for checking the centering of spectacles worn by a spectacle wearer is provided, comprising the steps:

a) measuring spectacle lenses mounted in a frame of the spectacles, wherein a position of permanent markings on the spectacle lenses is acquired relative to a coordinate system defined by frame rims by means of an image recognition system;

b) determining positions of nominal centering points, prescribed in a file, of the spectacle lenses in dependence on data of the spectacle lenses containing the position of the permanent markings;

measuring physiological data of a spectacle wearer wearing the spectacles and determining positions of actual centering points of the spectacle lenses from the physiological data by means of a video centering instrument;

d) determining the difference between the positions of the nominal centering points and the actual centering points; and e) comparing the difference to a prescribed difference threshold.

According to another aspect of the invention, an apparatus for checking spectacles worn by a spectacle wearer is provided, comprising:

a) first means for measuring spectacle lenses mounted in a frame of the spectacles, wherein the first means contain an image recognition system, by means of which a position of permanent markings on the spectacle lenses is acquired relative to a coordinate system defined by frame rims;

b) second means for determining positions of nominal centering points, prescribed in a file, of the spectacle lenses in dependence on data of the spectacle lenses containing the position of the permanent markings;

c) third means for measuring physiological data of a spectacle wearer wearing the spectacles and determining positions of actual centering points of the spectacle lenses from the physiological data, wherein the third means contain a video centering instrument;

d) fourth means for determining the difference between the positions of the nominal centering points and the actual centering points; and e) fifth means for comparing the difference to a prescribed difference threshold.

The object underlying the invention is completely achieved in this fashion.

This is because the invention allows checking of the centering of the spectacle lenses in a very simple, automated and reliable fashion. Hence further errors are ruled out.

In a preferred refinement of the method according to the invention, the coordinate system is derived from a box model of the spectacle lenses in step a).

The advantage of this measure is that it is possible to resort to a simple and established system.

It is furthermore preferred for an inner frame rim of the spectacles to be determined at the same time in step a) by the image recognition system.

The advantage of this measure is that the measurement can take place more quickly because two data records of interest are recorded at the same time.

A good effect is brought about if in step b) the data contains a frame-disk angle of the spectacle lenses.

The advantage of this measure is that the centering is also checked taking into account these further parameters.

In step b), the data preferably contain one item of information from the group: single-focus lens, multifocal lens, progressive lens.

Further advantages emerge from the description and the attached drawing.

It goes without saying that the aforementioned features and the features still to be explained below can be used not only in the respectively specified combination, but also in other combinations or on their own, without departing from the scope of the present invention.

BRIEF DESCRIPTION OF THE DRAWINGS

Exemplary embodiments of the invention are explained in more detail in the following description and are illustrated in the drawing, in which.

DETAILED DESCRIPTION OF PREFERRED EMBODIMENTS

In FIGS. 1A-1C, 10 denotes commercially available spectacles. The spectacles 10 have a right spectacle lens 12R and a left spectacle lens 12L. More particularly, the spectacle lenses 12R and 12L are progressive lenses.

The spectacle lenses 12R, 12L are respectively provided with two permanent markings 14R1, 14R2, 14L1, 14L2. These permanent markings 14R1, 14R2 and 14L1, 14L2 are usually produced by laser engraving and can usually just about be seen with the unaided eye. The permanent markings 14R1, 14R2 and 14L1, 14L2 have a defined position on the spectacle lenses 12R and 12L relative to the regions determined by the progressive characteristic. Said markings can furthermore contain information relating to the spectacle lens, for example an alphanumeric identification or another type of identification.

Furthermore, the spectacle lenses 12R and 12L each have far and near reference points. For a better understanding, these have been illustrated in FIG. 1A as far reference circle 16R and 16L and near reference circle 18R, 18L, which, it goes without saying, are not present on the actual spectacle lenses. The illustration as (open) far reference circle 16R and 16L and (closed) near reference circle 18R, 18L corresponds to the representation on templates provided to the opticians, who are undertaking manual centering, by the spectacle lens producers, as explained at the outset.

The spectacles 10 have a frame 20, which has been provided with frame rims 22R, 22L for the spectacle lenses 12R, 12L and with lateral side-pieces 24R, 24L and a nose piece 26.

Figure 1:
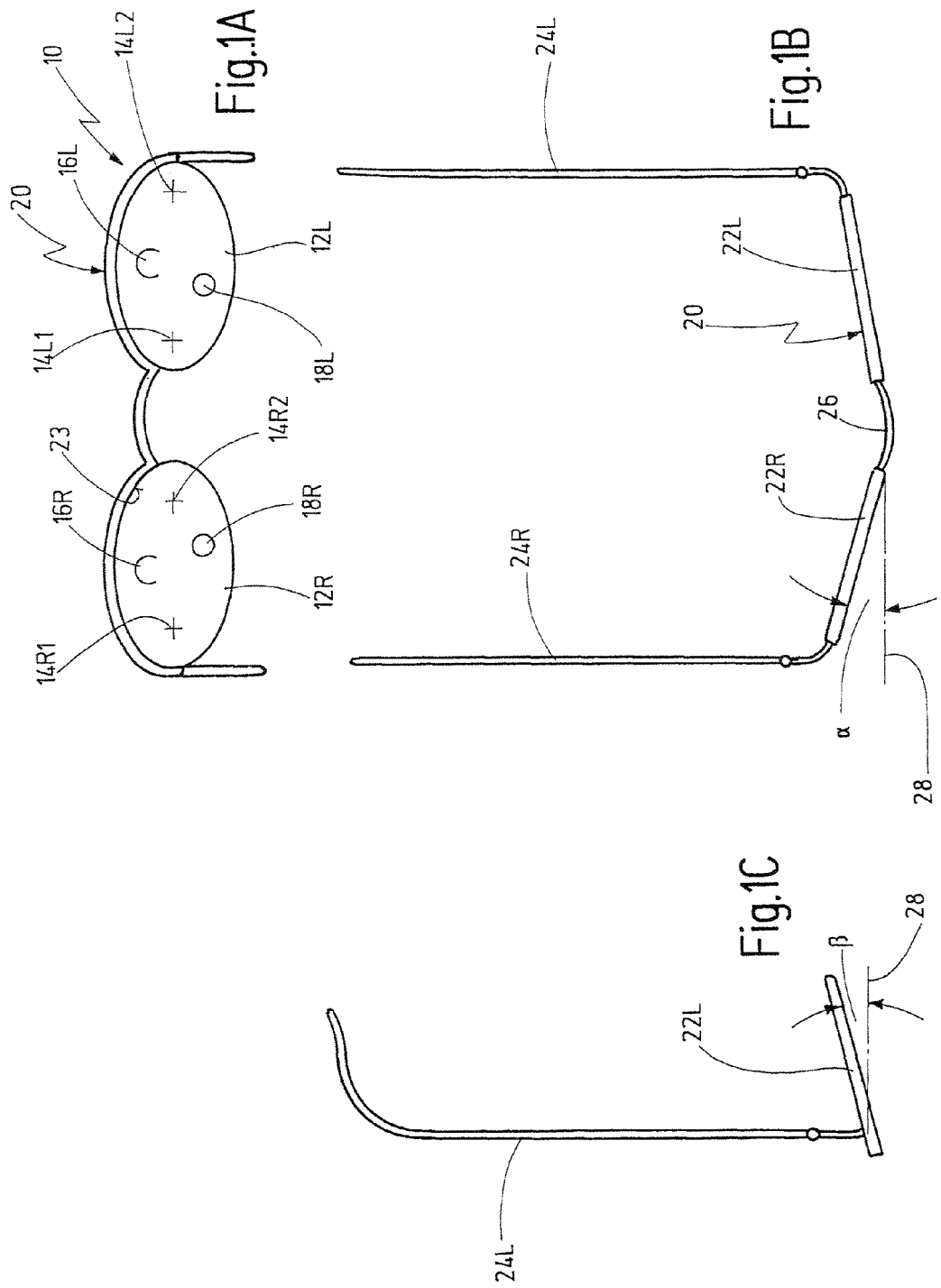
FIGS. 1A-1C show three views of spectacles for illustrating the measurement values of interest within the scope of the present invention.

In the illustrated example, the frame rims 22R, 22L with the spectacle lenses 12R, 12L are inclined relative to a frontal plane 28, to be precise by the so-called frame-disk angle, which is denoted by α relative to a horizontal axis in FIG. 1B and denoted by β relative to a vertical axis in FIG. 1C.

Figure 2:
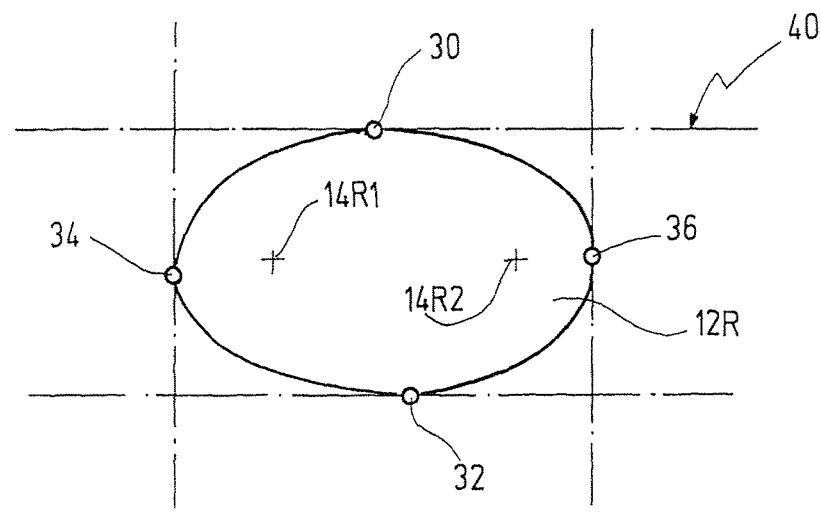
FIG. 2 shows an illustration of the so-called box model.

According to the invention the following procedure is carried out in order to check whether the position of the actual centering points of the spectacles 10 corresponds to the nominal centering points determined when fitting the spectacles:

The spectacle lenses 12R, 12L firstly are measured. To this end, FIG. 2 shows, in an exemplary fashion, for the right spectacle lens 12R that extreme points 30, 32, 34, 36 are determined at the top/bottom/left/right, from which the so-called box model is derived, which is indicated by 40 in FIG. 2. The position of the permanent engravings 14R1 and 14R2 is determined at the same time.

As a preferred option, the frame-disk angles α and β can also be measured in this step, and the positions of the permanent engravings 14R1 and 14R2, which are falsified in the frontal view as a result of these angles, can be corrected.

The inner frame rim 23 is established thereupon or at the same time.

As a first result, the position of the permanent markings 14R1, 14R2 are now available in an absolute reference system, specifically that of the frame rims 22R.

Figure 3:
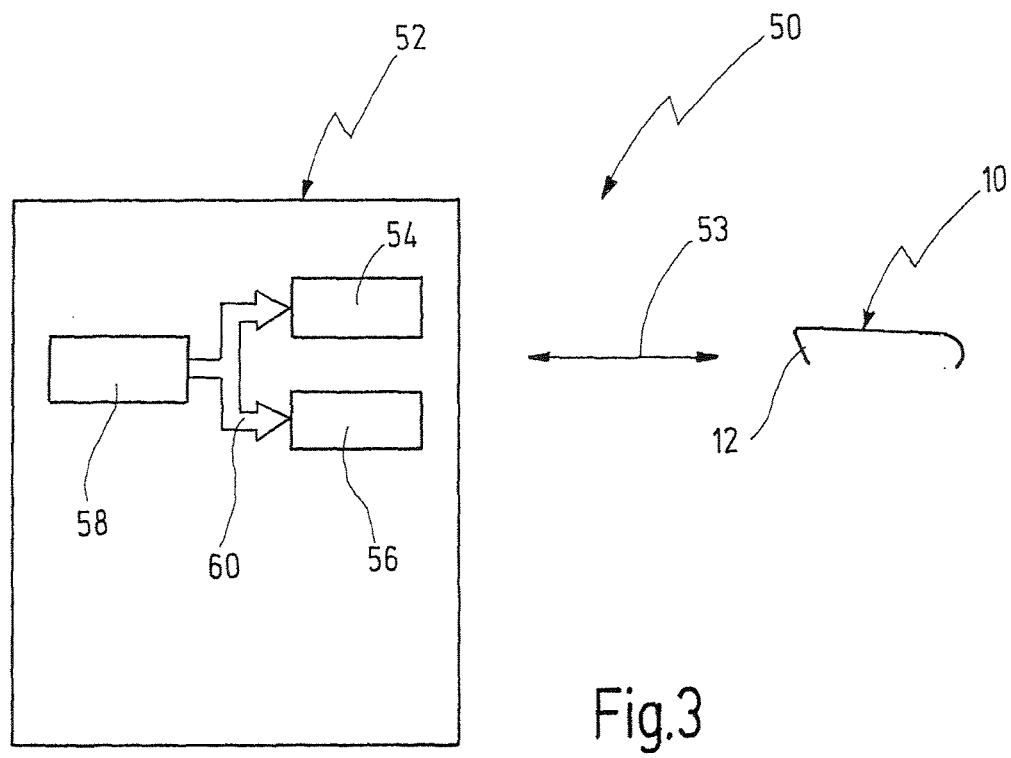
FIG. 3 shows a very schematized illustration of a measurement station, in which the apparatus according to the invention can be used.

This can be brought about in a measuring station 50, as illustrated in FIG. 3, by means of an apparatus 52 that optically interacts with the spectacles 10, as indicated by a double-headed arrow 53. The apparatus contains an image recognition system 54, for finding and determining the position of the permanent markings 14R1, 14R2, 14L1 and 14L2, and a video centering instrument 56, for measuring the spectacle lenses 12R, 12L and the frame-disk angles α and β.

The image recognition system 54 and the video centering instrument 56 are interconnected and connected to a calculation unit 58, for example via a data bus 60 or the like.

Together with the order data of the spectacles to be examined, the calculation unit 58 now determines the spectacle-lens type (single-focus lens, multifocal lens, progressive lens) of the spectacle lenses 12R, 12L and the nominal centering data from an integrated database or via remote querying of a central database. If need be, some of this data can also be read out directly from appropriately designed permanent markings 14R1, 14R2, 14L1, 14L2.

As a second result, the nominal centering data for the spectacle wearer and the spectacles 10 are now available.

The spectacle wearer now puts on the spectacles 10, and the physiological data required for the centering, more particularly the position of the centers of the pupils and the pupil spacing, are determined by means of the video centering instrument 56. In the process, a correction may be necessary because, unlike during the original fitting when the spectacles were ordered, when the frame was worn without spectacle lenses or with optically neutral spectacle lenses, the optically effective spectacle lenses 12R, 12L are now worn. The refraction of these spectacle lenses 12R, 12L also falsifies the measurement result in this case and therefore has to be compensated for by calculation if necessary. Furthermore, it is optionally possible to acquire the head posture of the spectacle wearer and this can, if need be, be used to derive a further correction, as is known per se.

As a third result, the actual centering data for the spectacle wearer and the spectacles 10 are now available.

Finally, the calculation unit 58 now compares the actual centering data with the nominal centering data and determines the difference in this data. This difference in turn is compared to a threshold, and, should the threshold be exceeded, a corresponding item of information is output. As an alternative, it is of course also possible to display the actual data and the nominal data, and it remains up to the user of the apparatus 52 to assess whether the deviation between the actual data and the nominal data is relevant.

The extent of the permissible deviation may either be fixedly prescribed, or it may be configured variably in dependence on other parameters. By way of example, the extent of the permissible deviation may be configured to be greater for weak spectacle lenses than for stronger spectacle lenses.

As illustrated in FIG. 3, the image recognition system 54 and the calculation unit 58 can be unified in a common apparatus 52. However, they can alternatively also be designed as separate units.

In embodiments of the invention, the image recognition system 54 can be combined with further units, for example with a lensmeter or a lens mapper. The refractive index or the refractive-index distribution can then be determined and checked directly. The combination with a blocker is also advantageous.

What is claimed is:

1. A method for checking actual centering points of spectacles worn by a spectacle wearer, the spectacles containing lenses having a refraction effect which are mounted in a frame having frame rims, comprising the steps of:
    a) measuring, by means of an image recognition system, the positions of permanent markings on the spectacle lenses relative to a coordinate system defined by the frame rims, wherein said measuring step is performed exclusively with image data of the spectacles only;
    b) determining relative to the position of said permanent markings, positions of nominal centering points, prescribed in a file of the spectacle lenses in dependence on data of the spectacle lenses containing the position of the permanent markings;
    c) measuring, by means of a video centering instrument, the position of the centers of the pupils and/or the pupil spacing of a spectacle wearer wearing the spectacles, corrected in accordance with the refraction effect of the lenses, and determining therefrom the positions of the actual centering points of the spectacle lenses relative to the coordinate system defined by the frame rims in step a);
    d) determining the difference between the positions of the nominal centering points and the actual centering points; and
    e) comparing the difference to a prescribed difference threshold.

2. The method of claim 1, characterized in that in step a) the coordinate system is derived from a box model of the spectacle lenses.

3. The method of claim 1, characterized in that in step a) an inner frame rim of the spectacles is determined at the same time by the image recognition system.

4. The method of claim 1, characterized in that in step b) the data contain a frame-disk angle of the spectacle lenses.

5. The method of claim 1, characterized in that in step b) the data contain one item of information from the group: single-focus lens, multifocal lens, progressive lens.

6. An apparatus for checking actual centering points of spectacles worn by a spectacle wearer, the spectacles containing lenses having a refraction effect which are mounted in a frame having frame rims, comprising:
    a) first means containing an image recognition system, for measuring the positions of permanent markings on the spectacle lenses relative to a coordinate system defined by the frame rims, wherein said measuring is performed exclusively with image data of the spectacles only;
    b) second means for determining relative to the position of said permanent markings, positions of nominal centering points, prescribed in a file of the spectacle lenses in dependence on data of the spectacle lenses containing the position of the permanent markings;
    c) third means for measuring the position of the centers of the pupils and/or the pupil spacing of a spectacle wearer wearing the spectacles, corrected in accordance with the refraction effect of the lenses, and determining therefrom the positions of the actual centering points of the spectacle lenses relative to the coordinate system defined by the frame rims established by said first means, wherein the third means contain a video centering instrument;
    d) fourth means for determining the difference between the positions of the nominal centering points and the actual centering points; and
    e) fifth means for comparing said difference to a prescribed difference threshold.

7. An apparatus for checking actual centering points of spectacles worn by a spectacle wearer, the spectacles containing lenses having a refraction effect which are mounted in a frame having frame rims, comprising:
    a) a spectacle measuring unit containing an image recognition system for measuring the positions of permanent markings on the spectacle lenses relative to a coordinate system defined by the frame rims, wherein said measuring is performed exclusively with image data of the spectacles only;
    b) a processing unit for determining relative to the position of said permanent markings, positions of nominal centering points, prescribed in a file of the spectacle lenses in dependence on data of the spectacle lenses containing the position of the permanent markings;
    c) a wearer measuring unit for measuring the position of the centers of the pupils and/or the pupil spacing of a spectacle wearer wearing the spectacles, corrected in accordance with the refraction effect of the lenses, and determining therefrom the positions of the actual centering points of the spectacle lenses relative to the coordinate system defined by the frame rims established by said spectacle measuring unit, wherein the wearer measuring unit contains a video centering instrument;
    d) a calculation unit for determining the difference between the positions of the nominal centering points and the actual centering points; and e) a comparing unit for comparing the difference to a prescribed difference threshold.

8. The method of claim 1, characterized in that in step a), the position of permanent markings on the spectacle lenses is acquired directly relative to the coordinate system defined by the frame rims, and in step c), the positions of the actual centering points of the spectacle lenses is determined directly relative to the coordinate system defined by the frame rims.

9. The apparatus of claim 6, characterized in that said first means acquires the position of permanent markings on the spectacle lenses directly relative to the coordinate system defined by the frame rims, and said third means determines the positions of the actual centering points of the spectacle lenses directly relative to the coordinate system defined by the frame rims.

10. The apparatus of claim 7, characterized in that said spectacle measuring unit acquires the position of permanent markings on the spectacle lenses directly relative to the coordinate system defined by the frame rims, and said wearer measuring unit determines the positions of the actual centering points of the spectacle lenses directly relative to the coordinate system defined by the frame rims.

* * * * *